United States Patent [19]

Meinert

[11] Patent Number: 5,244,924

[45] Date of Patent: Sep. 14, 1993

[54] DILUENT FOR PERFLUOROCARBONS EMPLOYED FOR RETINAL UNFOLDING (UNFOLDING PFCL) AND METHOD OF TREATMENT

[75] Inventor: Hasso Meinert, Ulm, Fed. Rep. of Germany

[73] Assignee: Adatomed Pharmazeutische und Medizintechnische Gesellschaft MBH, Munich, Fed. Rep. of Germany

[21] Appl. No.: 823,652

[22] Filed: Jan. 24, 1992

[30] Foreign Application Priority Data

Jan. 24, 1991 [DE] Fed. Rep. of Germany ....... 4101976

[51] Int. Cl.$^5$ ..................... A61M 1/00; A61K 31/02
[52] U.S. Cl. .................... 514/759; 514/672; 514/722; 514/757; 514/912; 564/510; 568/683; 570/134; 604/28; 604/49; 604/56
[58] Field of Search ............... 570/134; 514/759, 912, 514/672, 722, 757; 604/28, 49, 56; 564/510; 568/683

[56] References Cited

U.S. PATENT DOCUMENTS

| | | | |
|---|---|---|---|
| 4,490,351 | 12/1984 | Clark, Jr. | 424/5 |
| 4,609,663 | 9/1986 | York, Jr. | 514/278 |
| 4,795,423 | 1/1989 | Osterholm | 604/49 |
| 5,037,384 | 8/1991 | Chang | 604/28 |

OTHER PUBLICATIONS

Weast, Ed., *CRC Handbook of Chemistry and Physics,* CRC Press, Inc., Boca Raton, Fla., (1982), pp. C-320, C-328.

Primary Examiner—Richard L. Raymond
Assistant Examiner—Scott C. Rand
Attorney, Agent, or Firm—Keck, Mahin & Cate

[57] ABSTRACT

A diluent for perfluorocarbons used for retinal unfolding (unfolding PFCL), consisting of a perfluorocarbon (diluent PFCL), which has a low viscosity and is volatile at room temperature, with a boiling point between body temperature (about 38° C.) and 100° C., for removing residual quantities of unfolding PFCL from the eye after performance of a retinal unfolding treatment. A method of treatment consisting of introducing into an eye the above diluent for the above purpose.

4 Claims, No Drawings

DILUENT FOR PERFLUOROCARBONS EMPLOYED FOR RETINAL UNFOLDING (UNFOLDING PFCL) AND METHOD OF TREATMENT

FIELD OF INVENTION

The invention relates to a diluent for perfluorocarbons used in retinal unfolding (unfolding PFCL).

BACKGROUND OF INVENTION

The use of liquid perfluorocarbons as a treatment liquid (unfolding PFCL) is known to the prior art, e.g., from US-PS 4 490 391. Due to its high chemical stability and to densities in the range of 1.5-1.8 g/cm$^3$, PFCL can be used favorably in the treatment of retinal detachment or of a large tears in the retina. In retinal unfolding, the liquid PFCLs are introduced into the eye after removing the vitreous body; while the patient lies on his back, the density of these liquids causes the retina, or torn retina, to again press back against the choroid tissue of the eye. After a residence time of several hours the PFCL is aspirated and replaced by a different medium, e.g., methyl silicon oil. Reference is made to the following literature in this connection:

H. Lagua, K. Lucke, M. H. Foerster "Entwicklung und gegenwärtiger Stand der Silikonölchirurgie" (Development and current status of silicon oil surgery) in Klin. Mbl. Augenheilk, 192, 1988, pp. 277-283; A. Kampik "Prophylaxe and Behandlung der proliferativen Vitreoretinopathien" (Prophylaxis and treatment of proliferative vitreoretinopathies) in Z. prakt. Augenheilkd. 7 pp. 323-326 (1986); Stanley Chang, Emin Ozmert, Neal J. Zimmermann "Intraoperative Perfluorcarbon Liquids in the Management of Proliferative Vitreoretinopathy" in American Journal of Ophthalmology 106 (Dec. 1988) pp. 668-674; Stanley Chang, "Low Viscosity Liquid Fluorochemicals in Vitreous Surgery" in American Journal of Opthalmology 103 (January 1987) pp. 38-43; Anselm Kampik "Klinik and Pathogenese der Windenblütenablatio" (Clinical practice and pathogenesis of retinal detachment) in Z. prakt. Augenheilk. 4 (1983) pp. 371-378; Klaus Lucke "Vitreoretinale Chirurgie bei komplizierten Netzhautablösungen" (Vitreoretinal surgery in complicated retinal detachments) in Z. prakt. Augenheilkd. 9 (1988) pp. 137-147.

It has now become evident that the unfolding PFCL cannot be aspirated without residue. Residual quantities in the form of droplets remain in the eye. Over a longer period of time these droplets can result in damage to the vitreous body and the lens. Removal of the unfolding PFCL without residue is not easily achieved, inasmuch as perfluorocarbons cannot be removed with conventional solvents.

SUMMARY OF INVENTION

The goal of the invention, therefore, is to create an agent by means of which perfluorocarbons which are employed as unfolding liquids for retinal unfolding can be removed from the eye without residue (i.e. without leaving any residue).

This problem is solved by the invention by means of a diluent for perfluorocarbons used for the purpose of retinal unfolding (unfolding PFCLs), in the form of a perfluorocarbon of low viscosity (diluent PFCL) that is more volatile at room temperature than unfolding PFCLs, with a boiling point between body temperature (about 38° C.) and 100° C.

DETAILED DESCRIPTION OF PREFERRED EMBODIMENT

This diluent can be used advantageously as a solvent for the residues of unfolding PFCLs remaining in the eye. Perfluorocarbons can be dissolved in perfluorocarbon systems. In the invention, however, the solvent or diluent provided for the removal of the residual unfolding PFCLs from the eye is such that it can be introduced into the eye e.g. by means of a cannula and a hypodermic needle, in order to thereby remove the residual portions of the unfolding liquid, and exhibits a relatively low boiling point above body temperature and between 38° C. and 100° C. This diluent operates as a solvent for the residual quantities of the unfolding liquid employed for the purpose of retinal unfolding (unfolding PFCLs). Particularly when relatively unvolatile and viscous PFCLs exhibiting a low vapor pressure are employed, the residual portion of such PFCLs can be advantageously removed with the diluent according to the invention.

The residual quantities of unfolding PFCLs can thus be removed by introducing about 1 to 3 cm$^3$ diluent PFCL with a cannula and a hypodermic needle. During a residence time of only several minutes the residual quantities dissolve in the diluent. The mixture (or solution) can be aspirated over the same path by means of the cannula. Furthermore, the diluent according to the invention permits the mixture to vaporize and rapidly evaporate the diluent and the residual unfolding PFCLs, due to a low boiling point or high vapor pressure. The poorly volatile portions of the unfolding PFCL previously absorbed in the diluent are converted into the gas phase in accordance with the law of dilution.

If slight quantities of PFC molecules remain in the eye during the gas phase, they will be absorbed and thus leave the eye.

It is also possible to allow several minutes to pass after drawing off the diluent, in order to permit evaporation of the residual quantities of the diluent, along with the dissolved unfolding PFCL, at the temperature of the eye, and then to rerinse with an inert gas, for example nitrogen or a rare (inert) gas, or with air. This additional step permits the residual portion of PFC molecules to also be quickly removed from the eye.

The diluent can also be used as a solvent, in particular, for residual quantities of the unfolding PFCLs, as they are described in German patent application P 41 00 059.5.

Examples of a highly volatile PFCL of low viscosity which can be used as a diluent are perfluoroalkanes with at least 6 carbon atoms per molecule, particularly perfluorohexane (C$_6$F$_{14}$), with a boiling point of about 60° C., or perfluoroheptane (C$_7$F$_{16}$), with a boiling point of about 82° C. Also suitable are perfluorotrialkylamines, for example, perfluorotriethylamine (N(C$_2$F$_5$)$_3$), with a boiling point of about 70° C., or perfluorodialkylethers, for example perfluorodipropylether (C$_3$F$_7$—O—C$_3$F$_7$), with a boiling point of about 60° C.

The diluent can also be made available in a treatment system in which it used as a diluent PFCL in combination with an unfolding PFCL. Here the unfolding PFCL and the diluent PFCL are stored in separate containers and are thus held ready for the retinal unfolding treatment. When treatment is commenced, the unfolding PFCL and diluent PFCL are introduced into the eye.

What is claimed is:

1. A method of treating an eye for retinal detachment, comprising the steps of:
   (a) removing a vitreous body from the eye;
   (b) introducing into the eye at least one viscous, non-volatile perfluorocarbon liquid (unfolding PFCL) which causes the retina to again press back against choroid tissue of the eye;
   (c) removing the unfolding PFCL from the eye;
   (d) introducing into the eye at least one perfluorocarbon liquid (diluent PFCL), different from the unfolding PFCL introduced in step (b), having a low viscosity and volatile at room temperature, with a boiling point between 38° C. and 100° C.;
   (e) dissolving during a residence time, residual quantities of the unfolding PFCL into the diluent PFCL; and
   (f) aspirating the mixture of the diluent PFCL and the therein previously dissolved unfolding PFCL.

2. The method of claim 1, further comprising the step of:
   (g) waiting a predetermined time after the aspirating step in order to permit evaporation of residual quantities of the diluent, together with the dissolved unfolding PFCLs.

3. The method of claim 2, further comprising the step of:
   (h) rinsing the eye with an inert gas.

4. The method of claim 1, wherein 1 to 3 $cm^3$ of diluent PFCL are introduced into the eye.

* * * * *